United States Patent
Leppänen et al.

(10) Patent No.: US 7,036,356 B2
(45) Date of Patent: May 2, 2006

(54) METHOD AND APPARATUS FOR DEFINING WATER CONTENT OF A LIQUID

(75) Inventors: Jukka Leppänen, Klaukkala (FI); Matti Lyyra, Vantaa (FI); Lars Stormbom, Vantaa (FI)

(73) Assignee: Vaisala Oyj, Helsinki (FI)

( * ) Notice: Subject to any disclaimer, the term of this patent is extended or adjusted under 35 U.S.C. 154(b) by 65 days.

(21) Appl. No.: 10/477,557

(22) PCT Filed: May 15, 2002

(86) PCT No.: PCT/FI02/00417

§ 371 (c)(1),
(2), (4) Date: Feb. 2, 2004

(87) PCT Pub. No.: WO02/093147

PCT Pub. Date: Nov. 21, 2002

(65) Prior Publication Data

US 2004/0154384 A1   Aug. 12, 2004

(30) Foreign Application Priority Data

May 16, 2001  (FI) .................................. 20011040

(51) Int. Cl.
G01N 33/20 (2006.01)
G01N 37/00 (2006.01)

(52) U.S. Cl. .................... 73/61.43; 73/61.46; 73/75

(58) Field of Classification Search ............... 73/61.46, 73/152.33, 204.11, 204.27; 374/54
See application file for complete search history.

(56) References Cited

U.S. PATENT DOCUMENTS

| | | | |
|---|---|---|---|
| 4,080,837 A | | 3/1978 | Alexander et al. |
| 4,221,125 A | * | 9/1980 | Oliver et al. ............... 73/61.46 |
| 4,891,969 A | | 1/1990 | Wayland et al. |
| 5,330,268 A | | 7/1994 | Klein et al. |
| 5,415,024 A | * | 5/1995 | Proffitt et al. ............... 73/61.44 |
| 5,563,337 A | | 10/1996 | Fitch et al. |
| 5,597,961 A | | 1/1997 | Marrelli |

FOREIGN PATENT DOCUMENTS

| | | |
|---|---|---|
| EP | 0 208 096 A1 | 1/1987 |
| EP | 0208096 A1 | 1/1987 |
| EP | 0 417 936 A2 | 3/1991 |

OTHER PUBLICATIONS

Patent Abstract of Japan: vol. 199, No. 29 Jan. 1999 & JP 10282084 A (MITSUI SHIP BUILDING ENG). (Oct. 23, 1998).

* cited by examiner

*Primary Examiner*—Charles Garber
(74) *Attorney, Agent, or Firm*—Birch, Stewart, Kolasch & Birch, LLP

(57) ABSTRACT

The invention relates to a method and apparatus for measurement of total water content in a liquid. According to the method, the relative water content (aw) of the liquid is measured in a first measurement step at a first temperature $(T_1)$. According to the invention, the temperature of the liquid under measurement is altered from the first temperature $(T_1)$ and the relative water content is measured in a second measurement step at the second, altered temperature $(T_2)$, whereby, based on these at least two measurement values $(aw(1)T_1, aw(2)T_2)$, the total water content is determined from the temperature dependence of water dissolution into the liquid under measurement.

17 Claims, 4 Drawing Sheets

US 7,036,356 B2

METHOD AND APPARATUS FOR DEFINING WATER CONTENT OF A LIQUID

This application is the national phase under 35 U.S.C. § 371 of PCT International Application No. PCT/FI02/00417 which has an International filing date of May 15, 2002, which designated the United States of America.

BACKGROUND OF THE INVENTION

Field of the Invention

The invention relates to a method for measuring the water content of a liquid.

The invention also relates to an apparatus for measuring the water content of a liquid.

The invention also relates to an apparatus according to claim 7 for measuring the water content of a liquid.

Due to phase changes of water, it has turned out problematic to measure the water content of liquid materials such as kerosine, lubricants or hydraulic fluids. Current methods permit water content measurement only from one phase of the water-containing system or detect total water content without distinction between the phases. Furthermore, the phase system subject to measurement is frequently in a dynamic state, whereby a steady-state equilibrium between water and the other liquid phase has not been attained. As a result, distribution between the different phases (formation of free water) cannot be predicted reliably from the total water content or, conversely, the total water content cannot be determined on the basis of measurements performed on a single phase only.

SUMMARY OF THE INVENTION

It is an object of the present invention to overcome the problems of the prior-art techniques and to provide an entirely novel type of method and apparatus for determining the water content of a liquid material.

The goal of the invention is achieved based on a novel concept that, since conventional techniques permit the measurement of the dissolved amount of water only, the present invention utilizes the positive temperature dependence of water content, which is characteristic of hydrophobic liquids, in such a fashion that the temperature of the sample under measurement is elevated until all free water is dissolved. Knowing the temperature dependence of water content in the sample a priori or as determined from a cooling curve of the sample, the water content can be computed for each phase separately, whereby also the total water content is obtained. According to a preferred embodiment of the invention, the temperature of the sample under measurement is varied in a cyclic fashion. According to another preferred embodiment, the sample is divided into a heatable bypass flow, while the reference measurement is performed on the main flow. In a third preferred embodiment, the measurement is based on a sampling technique.

More specifically, the method according to the invention alters the temperature of the liquid under measurement from a first temperature ($T_1$) and the relative water content is measured at a second, altered temperature ($T_2$) in a second measurement step, and based on these at least two measurement values (aw((1)$T_1$, aw(2)$T_2$), the total water content is determined from the temperature dependence of water dissolution into said liquid under measurement.

Furthermore, the apparatus according to the method includes means (7, 8) for altering the temperature of the liquid under measurement from said first temperature ($T_1$) and means for measuring the relative water content at said second, altered temperature ($T_2$), and computing means (8) for determination of the total water content on the basis of these at least two measurement values (taken at $T_1$, $T_2$) utilizing the temperature dependence of water dissolution into said liquid.

The invention offers significant benefits.

The invention offers a reliable technique for determination of total water content of a liquid. Also the amounts of water distributed in the different phases of the liquid can be determined by virtue of the invention. Measurements can be carried out in a continuous fashion or on discrete samples.

BRIEF DESCRIPTION OF THE DRAWING FIGURES

In the following, the invention will be examined in more detail by means of exemplifying embodiment(s) illustrated in the appended drawings, in which.

DETAILED DESCRIPTION

Figure 1:
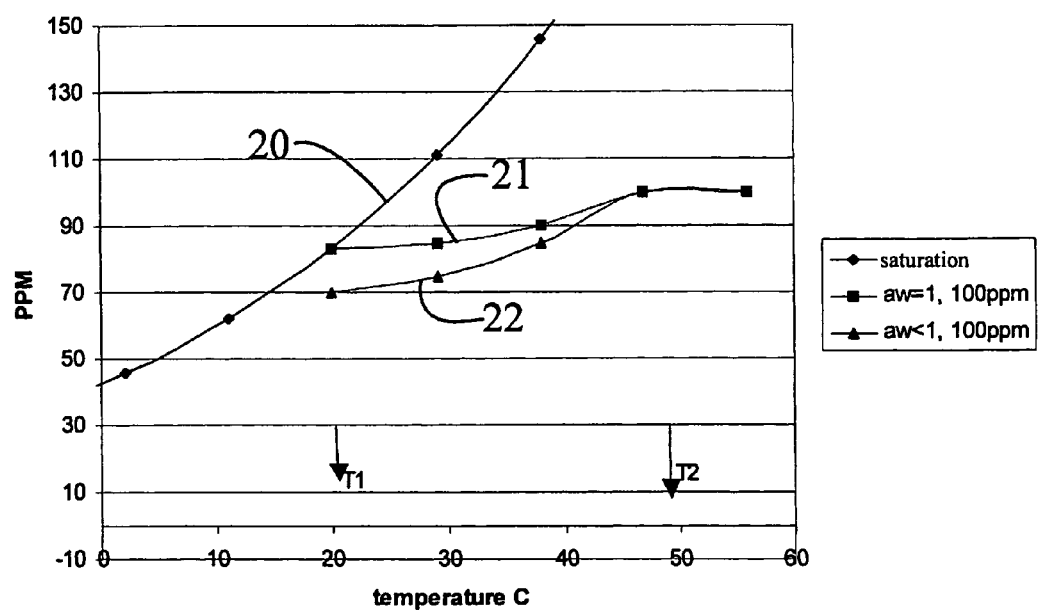
FIG. 1 shows a graph illustrating an embodiment of a measurement cycle according to the invention.

Assuming that the liquid under measurement can be characterized by a mathematical model capable of describing the behavior of water in the liquid as a function of temperature, the invention provides a computational technique for the determination of the contents of total water, free water and dissolved water in the liquid. In FIG. 1 are shown graphs illustrating two exemplary cases plotted with the vertical axis as the absolute water content in ppm and the horizontal axis as the temperature of the liquid under measurement. Curve 20 shows the water content saturation point as a function of temperature, in other words, permitting curve 20 to be used for determining the maximum water content that the liquid in question can bind in dissolved phase at a given temperature. Curves 21 and 22 are two measured curves for samples having the same total water content but different proportions of dissolved and undissolved water at a given temperature $T_1$. Curve 21 shows a situation wherein the sample at a temperature $T_1$ has reached the saturation curve 20, which means that the relative water content aw is 1. Now, when the sample is heated, the decreasing value of the measured relative water content aw can be used for computing the absolute value of water content that on curve 21 rises from 83 ppm to 100 ppm at a temperature $T_2$. The increase of the measured value is caused by the dissolution of free water into the liquid under measurement. After this point, the absolute water content computed from the value of relative water content aw does not continue to increase, which means that all the water contained in the liquid sample may be assumed to be in a dissolved phase. The difference (about 17 ppm) of water contents at temperatures $T_1$ and $T_2$ represents the amount of undissolved water. Hence, the termination point of measurement, e.g., at temperature $T_2$ may be defined as a point at which no more increase in the computed absolute value of water content occurs as a result of increased temperature. Inasmuch aw<1 in the case of curve 22, the sample is not in an equilibrium state when the measurement is started at temperature $T_1$. When the second sample is heated to temperature $T_2$, curves 21 and 22 coincide giving the same termination point of 100 ppm absolute water content for both samples. Using the same computational technique as for curve 21, the amount of undissolved water is about 30 ppm for the sample of curve 22.

Accordingly, the computations may be based on equations:

$PPMtot=PPM(T2)$ $PPMsol=PPM(T1)$ $PPMfw=PPM(T2)-PPM(T1)$, where

PPMtot=total water content
PPMsol=amount of dissolved water
PPMfw=amount of free water (i.e., undissolved water).

The progress of water dissolution can be followed by comparing the ppm values of water content obtained at increasing temperature. As long as the ppm value grows, free water is still in undissolved state.

Figure 2A:
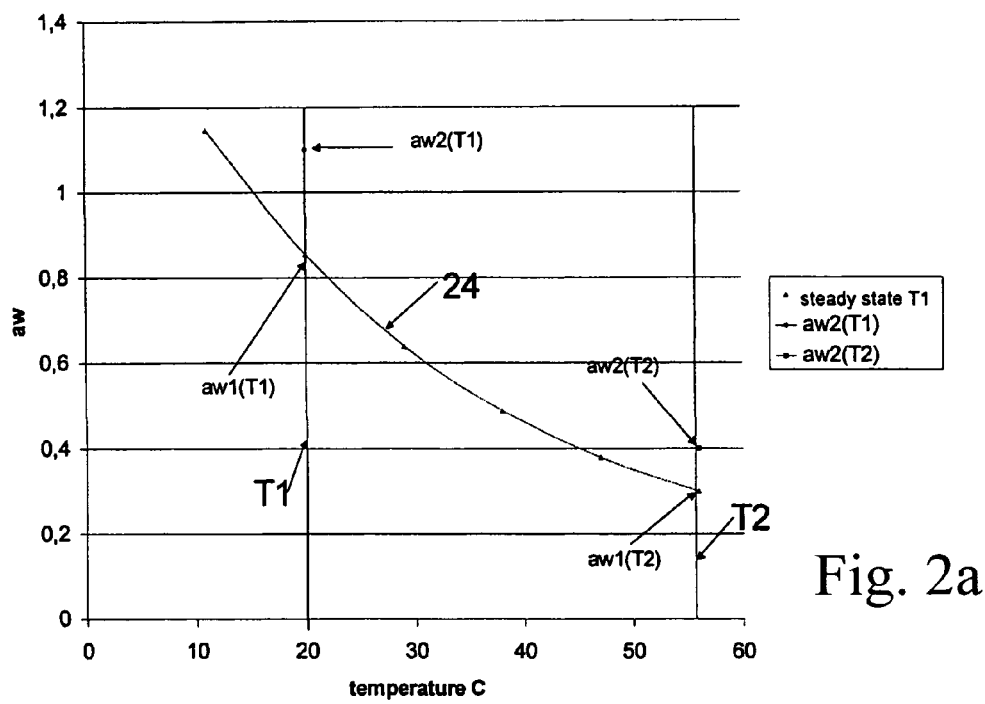
FIG. 2a shows a graph of a second embodiment of a measurement cycle according to the invention.
Figure 2B:
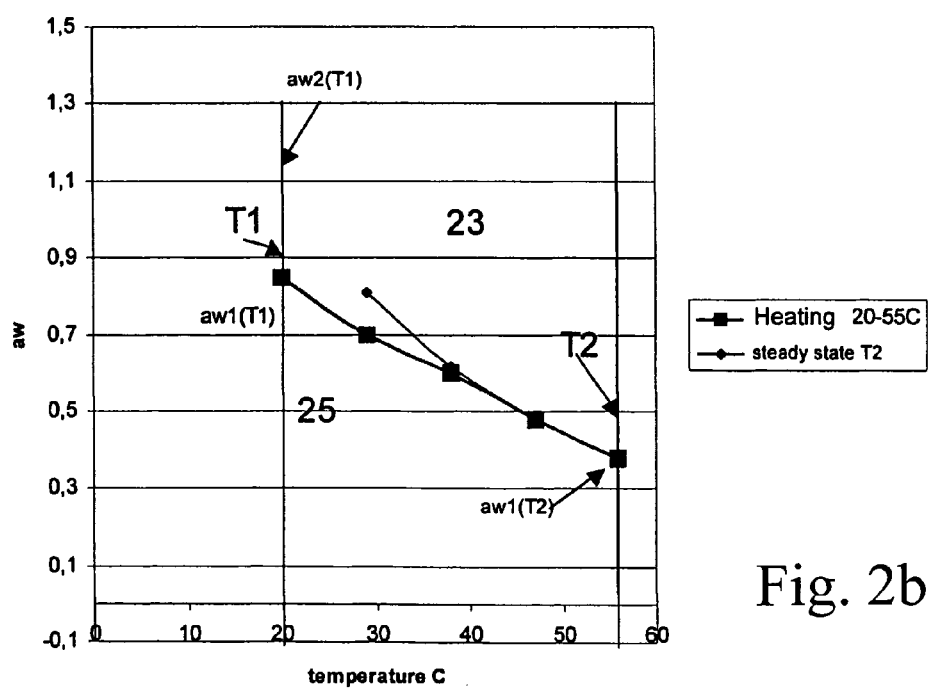
FIG. 2b shows a graph of a third embodiment of a measurement cycle according to the invention.

If the ppm model describing the dependence of absolute water content as a function of relative water content is not known, an alternative approach is to utilize the values of relative water content (aw) obtained at two selected temperatures $T_1$, $T_2$ and therebetween in the fashion illustrated in FIGS. 2a and 2b. Curve 24 of FIG. 2a is measured by way of heating the sample so rapidly that no dissolution of free water into the sample can take place. This procedure assures that the absolute amount of dissolved water in the sample stays constant while the relative water content (aw) has fallen as determined by its temperature dependence. After all free water has dissolved at temperature $T_2$ (as detected from no longer increase in the aw value), the measurement cycle may be terminated at point $aw2(T_2)$ for the determination of the relative proportion of free water and the computation of the same (free water) at temperature $T_1$ as follows:

$$\frac{aw1(T2)}{aw2(T2)}*aw1(T1)=aw2(T1)$$

The relative value of total water content in regard to its saturation value is obtained from equation:

$aw2(T1)*100\%$ and, respectively, the proportion of free water is obtained from equation:

$aw2(T1)-aw1(T1)$.

As illustrated in FIG. 2b, an alternative method is to determine the temperature dependence from cooling curve 23 of the phase "model". First, the sample is heated along curve 25 to temperature $T_2$ and is subsequently allowed to cool toward temperature $T_1$. Next, from cooling curve 23 are selected at least two measurement points of temperature vs. aw value (with the precondition that aw>1), whereby these values can be used for determining the coefficients of the temperature dependence equation. Using the same equation, it is further possible to compute the values of the above-mentioned variables at temperature $T_1$.

The measurement apparatus may be calibrated using oil-specific coefficients. Herein, the water content of a given oil composition must predetermined by titration or known by other means. Then, the measurement apparatus can update the coefficients by computation based on the water content values $aw(1)T_1$ and $aw(2)T_2$ entered to the apparatus.

Figure 3:
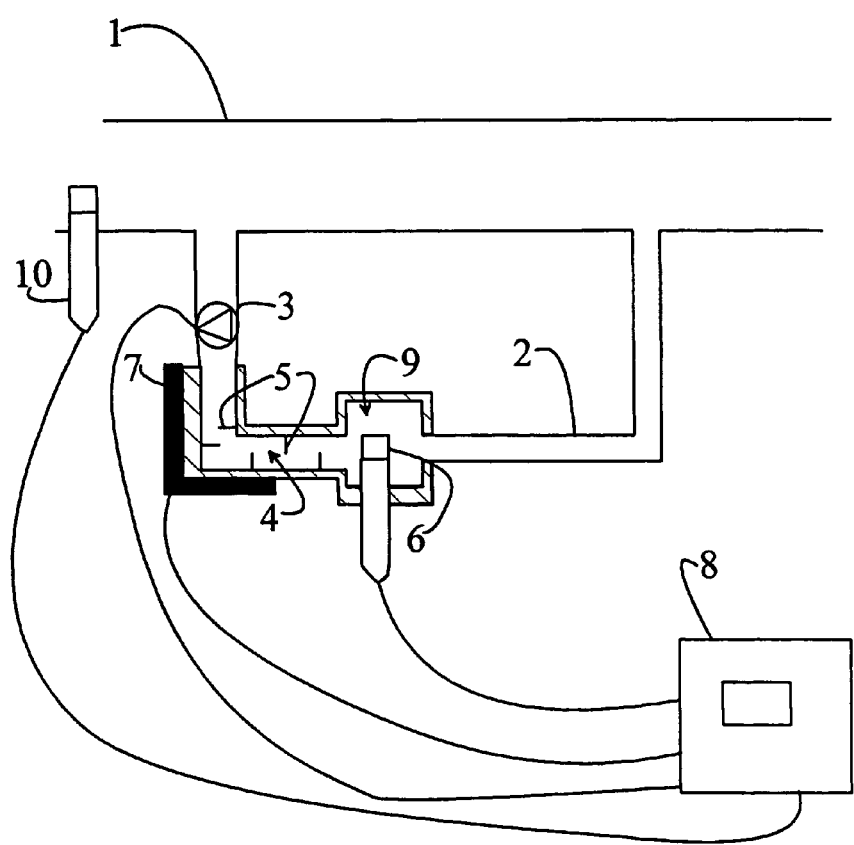
FIG. 3 shows diagrammatically a continuously-operating measurement apparatus according to the invention.

As shown in FIG. 3, the measurement apparatus can be implemented as a bypass sensor that performs the measurements in a continuous fashion. The main flow pipe 1 is provided with a bypass flow channel 2 either as an unassisted free-flow or, alternatively, forced by a pump 3. The pump 3 may be controlled individually by the control block of measurement apparatus 8. To the bypass channel 2 is adapted a flow duct 4 heatable by means of a heater 7 that also is controlled by the control block of measurement apparatus 8. In the flow duct 4 are mounted mixing baffles 5 serving to mix the liquid under measurement and increase the length of its flow path in order to improve the heating of the fluid. Next to the flow duct 4 is located a measurement chamber 9 having a measurement transducer 6 located therein. Typically, the measurement transducer 6 is a sensor of relative humidity, such as a capacitive humidity sensor based on a dielectric polymer material. The output signal of transducer 6 is taken to measurement apparatus 8. Typically, the measurement data supplied by transducer 6 comprises a measurement signal of the relative water content aw and a temperature measurement signal. When necessary, the measurement apparatus 8 may have connected thereto also a second measurement transducer 10 serving to provide in accordance with the methods described above a second measurement signal taken at a different temperature, generally at a temperature substantially close to the ambient temperature. Typically, measurement transducer 10 submits in the above-described fashion both the relative humidity and the temperature signals. Obviously, these two signals may also be taken from respective dedicated transducers that are located sufficiently close to each other. In addition to the measurement and control functions, measurement apparatus 8 generally also includes the computational facilities required for conversion of measurement signals into desired formats. Generally, a conversion is made from a relative value to an absolute value. According to an alternative embodiment, the liquid entering the measurement chamber 9 may be subjected to cyclic heating and cooling. Cooling may take place in a passive manner by switching off the heater or, alternatively, actively through using a Peltier element (not shown), for instance. The measurement apparatus illustrated in the diagrams can be connected, e.g., to a discharge pipe of a storage yard of liquids, a discharge pipe of a fuel tank truck or, in kerosine measurements, possibly to the infeed pipe of an airplane as a precautionary measure.

Figure 4:
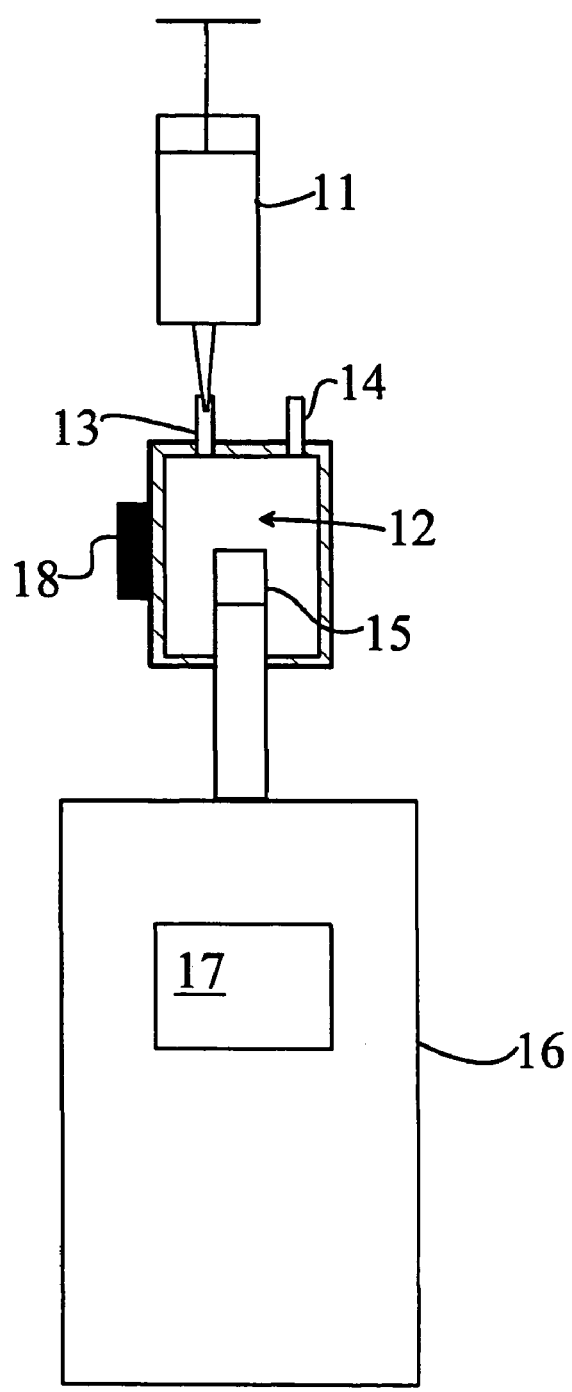
FIG. 4 shows diagrammatically a sampling measurement apparatus according to the invention.

As shown in FIG. 4, the measurement apparatus may also be implemented as a portable sampling device 16, wherein the liquid to be analyzed is sampled, e.g., with the help of an injection syringe 11, wherefrom the sample is injected via an infeed pipe 13 into a measurement chamber 12. The measurement chamber is equipped with a heater 18 and possibly complemented with a cooler. The above-described measurement is then carried out using the measurement apparatus and the readings are logged from a display 17. After the measurement cycle is completed, the sample can be discarded via a discharge pipe 14.

It must be understood that the foregoing description of the invention as used in conjunction with liquids having a positive temperature coefficient of water dissolution coefficient does not limit the applications of the invention that may as well be applied to liquids having a negative dissolution coefficient. Furthermore, the invention elucidated above can be used equally well in continuously operating measurement systems shown in FIG. 3 as in a sampling measurement system illustrated in FIG. 4.

What is claimed is:

1. A method for measurement of total water content in a liquid, which comprises:
   measuring a relative water content (aw) of the liquid in a first measurement step at a first temperature ($T_1$),
   altering the temperature of the liquid from said first temperature ($T_1$),
   measuring the relative water content at said second, altered temperature ($T_2$) in a second measurement step, and
   based on these at least two measurement values (aw(1)$T_1$, aw(2)$T_2$),
   determining a total water content from the temperature dependence of water dissolution into said liquid under measurement.

2. The method of claim 1, wherein the liquid under measurement is heated for the second measurement step.

3. The method of claim 1, wherein the liquid under measurement is heated so long that its relative water content ceases to increase and up to such an elevated temperature that the stabilized value of water content is less than 1 aw, whereby the entire amount of water in the sample is dissolved into the liquid under measurement.

4. The method of claim 1, wherein the first and the second measurement steps are at least substantially performed as a continuous measurement.

5. The method of claim 1, wherein the first and the second measurement steps are utilized for determination of the relative proportion of water in each phase of the liquid at ambient temperature.

6. The method of claim 1, wherein the sample of liquid to be heated and the sample of liquid to be measured at ambient temperature is the same sample.

7. An apparatus for measurement of total water content in a liquid, the apparatus comprising a transducer (6) for measuring the relative water content (aw) of the liquid in a first measurement step at a first temperature ($T_1$),
   wherein the apparatus includes a device (7, 8) for altering the temperature of the liquid under measurement from said first temperature ($T_1$) and a transducer for measuring the relative water content at said second, altered temperature ($T_2$), and
   computing means a computer (8) for determination of the total water content on the basis of these at least two measurement values (taken at $T_1$, $T_2$) utilizing the temperature dependence of water dissolution into said liquid.

8. The apparatus of claim 7, wherein the apparatus includes at least one of a heater or a Peltier.

9. The apparatus of claim 7, wherein the measurement apparatus is a continuously operating measurement system.

10. The apparatus of claim 7, wherein the measurement apparatus (8) includes a device for determination of the amount of water in each phase of the liquid as a relative proportion in regard to the total water content.

11. The method of claim 2, wherein the liquid under measurement is heated so long that its relative water content ceases to increase and up to such an elevated temperature that the stabilized value of water content is less than 1 aw, whereby the entire amount of water in the sample is dissolved into the liquid under measurement.

12. The method of claim 2, wherein the first and the second measurement steps are at least substantially performed as a continuous measurement.

13. The method of claim 3, wherein the first and the second measurement steps are at least substantially performed as a continuous measurement.

14. The apparatus of claim 8, wherein the measurement apparatus is a continuously operating measurement system.

15. The method of claim 1, wherein the temperature is altered using a heater or a Peltier.

16. The method of claim 1, wherein the temperature is measured using a capacitive humidity sensor comprising a dielectric polymer material.

17. The apparatus of claim 7, wherein each transducer is a capacitive humidity sensor comprising a dielectric polymer material.

* * * * *